(12) United States Patent
Wilkinson et al.

(10) Patent No.: US 11,793,432 B2
(45) Date of Patent: Oct. 24, 2023

(54) BIOLOGICAL FLUID COLLECTION DEVICE AND BIOLOGICAL FLUID COLLECTION SYSTEM

(71) Applicant: Becton, Dickinson and Company, Franklin Lakes, NJ (US)

(72) Inventors: Bradley M. Wilkinson, North Haledon, NJ (US); C. Mark Newby, Kamas, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 322 days.

(21) Appl. No.: 17/151,531

(22) Filed: Jan. 18, 2021

(65) Prior Publication Data
US 2021/0128038 A1     May 6, 2021

Related U.S. Application Data

(63) Continuation of application No. 15/228,280, filed on Aug. 4, 2016, now Pat. No. 10,925,532.
(Continued)

(51) Int. Cl.
*A61B 5/15* (2006.01)
*A61B 5/151* (2006.01)
*A61B 5/155* (2006.01)

(52) U.S. Cl.
CPC ........ *A61B 5/150755* (2013.01); *A61B 5/155* (2013.01); *A61B 5/150022* (2013.01); *A61B 5/15105* (2013.01); *A61B 5/15117* (2013.01); *A61B 5/15198* (2013.01); *A61B 5/150213* (2013.01); *A61B 5/150221* (2013.01); *A61B 5/150267* (2013.01); *A61B 5/150389* (2013.01);
(Continued)

(58) Field of Classification Search
CPC ........ A61B 5/150755; A61B 5/150267; A61B 5/150389; A61B 5/15117
See application file for complete search history.

(56) References Cited

U.S. PATENT DOCUMENTS 3,322,114 A   5/1967   Portnoy et al.
3,640,393 A   2/1972   Hurtig
(Continued)

FOREIGN PATENT DOCUMENTS

DE   202008010918 U1   12/2008
EP       0376168 A2   7/1990
(Continued)

*Primary Examiner* — Alex M Valvis
*Assistant Examiner* — Yasmeen S Warsi
(74) *Attorney, Agent, or Firm* — The Webb Law Firm

(57) ABSTRACT

A biological fluid collection device that is adapted to receive a blood sample is disclosed. The biological fluid collection device includes a housing, a puncturing element transitionable between a pre-actuated position wherein the puncturing element is retained within the housing and a puncturing position wherein at least a portion of the puncturing element extends through the housing, and a cartridge removably connectable to a portion of the housing. After collecting a blood sample, the cartridge is removable from the housing and the cartridge is able to transfer the blood sample to a point-of-care testing device. The biological fluid collection device provides a closed system that reduces the exposure of a blood sample and provides fast mixing of a blood sample with a sample stabilizer.

11 Claims, 22 Drawing Sheets

Related U.S. Application Data

(60) Provisional application No. 62/201,763, filed on Aug. 6, 2015.

(52) U.S. Cl.
CPC .. *A61B 5/150786* (2013.01); *A61B 5/150793* (2013.01); *A61B 5/150969* (2013.01)

(56) References Cited

U.S. PATENT DOCUMENTS

| | | | |
|---|---|---|---|
| 4,627,445 A | 12/1986 | Garcia et al. | |
| 5,046,509 A | 9/1991 | Kater | |
| 5,055,203 A | 10/1991 | Columbus | |
| 5,137,521 A | 8/1992 | Wilkins | |
| 5,231,993 A | 8/1993 | Haber et al. | |
| 5,356,392 A | 10/1994 | Firth et al. | |
| 5,636,640 A | 6/1997 | Staehlin | |
| 5,726,026 A | 3/1998 | Wilding et al. | |
| 6,074,183 A | 6/2000 | Allen et al. | |
| 6,241,886 B1 | 6/2001 | Kitagawa et al. | |
| 6,319,719 B1 | 11/2001 | Bhullar et al. | |
| 6,350,412 B1 * | 2/2002 | Williams | G01N 35/10 422/65 |
| 6,506,167 B1 | 1/2003 | Ishimito et al. | |
| 8,561,795 B2 | 10/2013 | Schott | |
| 8,808,202 B2 | 8/2014 | Brancazio | |
| 8,827,971 B2 | 9/2014 | Gonzalez-Zugasti et al. | |
| 9,119,578 B2 | 9/2015 | Haghgooie et al. | |
| 9,295,417 B2 | 3/2016 | Haghgooie et al. | |
| 9,549,700 B2 | 1/2017 | Fletcher et al. | |
| 2002/0009015 A1 | 1/2002 | Laugharn, Jr. et al. | |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0106552 A1 | 5/2005 | Ikeda | |
| 2005/0273019 A1 | 12/2005 | Conway et al. | |
| 2006/0029923 A1 | 2/2006 | Togawa et al. | |
| 2006/0224172 A1 | 10/2006 | LeVaughn et al. | |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0204026 A1 | 8/2009 | Crawford et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0009891 A1 | 1/2011 | Stout et al. | |
| 2011/0124130 A1 | 5/2011 | Wagner et al. | |
| 2011/0124984 A1 | 5/2011 | Rostaing | |
| 2012/0118825 A1 | 5/2012 | Margraf et al. | |
| 2012/0152858 A1 | 6/2012 | Yang | |
| 2012/0277696 A1 | 11/2012 | Gonzalez-Zugasti et al. | |
| 2012/0277697 A1 | 11/2012 | Haghgooie et al. | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |
| 2014/0166514 A1 | 6/2014 | Martin et al. | |
| 2014/0305196 A1 | 10/2014 | Ellis et al. | |
| 2014/0305197 A1 | 10/2014 | Fletcher et al. | |
| 2014/0305823 A1 | 10/2014 | Gelfand et al. | |
| 2014/0308164 A1 | 10/2014 | Wilkinson et al. | |
| 2014/0308165 A1 | 10/2014 | Marchiarullo et al. | |
| 2014/0308166 A1 | 10/2014 | Fletcher et al. | |
| 2014/0308167 A1 | 10/2014 | Fletcher et al. | |
| 2014/0308179 A1 | 10/2014 | Marchiarullo et al. | |
| 2014/0309096 A1 | 10/2014 | Wilkinson et al. | |
| 2014/0309551 A1 | 10/2014 | Burkholz et al. | |
| 2014/0309555 A1 | 10/2014 | Gelfand et al. | |
| 2014/0309556 A1 | 10/2014 | Fletcher et al. | |
| 2014/0309558 A1 | 10/2014 | Fletcher et al. | |
| 2017/0049372 A1 | 2/2017 | Gelfand et al. | |

FOREIGN PATENT DOCUMENTS

| | | | |
|---|---|---|---|
| EP | 747006 A1 * | 12/1996 | ........... A61B 5/1411 |
| EP | 0747105 A2 | 12/1996 | |
| EP | 1096254 A2 | 5/2001 | |
| EP | 1106065 A2 | 6/2001 | |
| EP | 1477804 A1 | 11/2004 | |
| EP | 1602329 A1 | 12/2005 | |
| EP | 1627651 A2 | 2/2006 | |
| EP | 2264453 A1 | 12/2010 | |
| EP | 2413138 A2 | 2/2012 | |
| EP | 3281703 A1 * | 2/2018 | ........... A61B 5/1411 |
| EP | 3281703 A1 | 2/2018 | |
| FR | 2929135 A1 | 10/2009 | |
| FR | 2977808 A1 | 1/2013 | |
| JP | 196514 U | 6/1989 | |
| JP | 6237922 A | 8/1994 | |
| JP | 10241784 A | 9/1998 | |
| JP | 2004361419 A | 12/2004 | |
| WO | 9309710 A1 | 5/1993 | |
| WO | 2005018710 A2 | 3/2005 | |
| WO | 2006047831 A1 | 5/2006 | |
| WO | 2007002579 A2 | 1/2007 | |
| WO | 2009123592 A1 | 10/2009 | |
| WO | 2011040874 A1 | 4/2011 | |
| WO | 2012121686 A1 | 9/2012 | |
| WO | 2014172235 A1 | 10/2014 | |
| WO | 2014172238 A1 | 10/2014 | |
| WO | 2014172242 A1 | 10/2014 | |
| WO | 2014172243 A1 | 10/2014 | |
| WO | 2014172245 A1 | 10/2014 | |
| WO | 2014172246 A1 | 10/2014 | |
| WO | 2014172247 A1 | 10/2014 | |
| WO | WO-2014172238 A1 * | 10/2014 | ........... A61B 5/1411 |

\* cited by examiner

BIOLOGICAL FLUID COLLECTION DEVICE AND BIOLOGICAL FLUID COLLECTION SYSTEM

CROSS REFERENCE TO RELATED APPLICATIONS

The present application is a continuation of U.S. patent application Ser. No. 15/228,280 filed Aug. 4, 2016, which claims priority to U.S. Provisional Application No. 62/201,763 filed Aug. 6, 2015, the entire disclosures of each of which are herein incorporated by reference.

BACKGROUND OF THE INVENTION

Field of the Disclosure

The present disclosure relates generally to devices, assemblies, and systems adapted for use with vascular access devices. More particularly, the present disclosure relates to devices, assemblies, and systems adapted for collecting biological samples for use in point of care testing.

Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, and coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process. Furthermore, mixing with an anticoagulant or other component to stabilize the sample must be performed manually.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device that is adapted to receive a blood sample. In accordance with an embodiment of the present invention, the biological fluid collection device includes a housing having a receiving port and an inlet port. The inlet port defines a housing flow channel therein in fluid communication with the inlet port. A puncturing element is at least partially disposed within the housing and transitionable between a pre-actuated position wherein the puncturing element is retained within the housing and a puncturing position wherein at least a portion of the puncturing element extends through the inlet port of the housing for establishing fluid communication with the housing flow channel. A cartridge defining a cartridge flow channel is removably connectable to the receiving port of the housing. With the cartridge connected to the housing, the cartridge flow channel is in fluid communication with the housing flow channel and with the cartridge disconnected from the housing, the cartridge flow channel is sealed. The housing flow channel of the biological fluid collection device is adapted to receive a multi-component blood sample having a cellular portion and a plasma portion.

In one configuration, a sample stabilizer is disposed within a portion of the cartridge flow channel. A separation member may be disposed at least partially within a portion of the cartridge flow channel. The separation member is configured to restrain the cellular portion and allow the plasma portion to pass therethrough.

In one configuration, the cartridge includes a cartridge inlet port in fluid communication with the housing flow channel when the cartridge is received within the receiving port of the housing and a transfer port in fluid communication with the cartridge flow channel. The cartridge flow channel may include a serpentine shape. With the cartridge disconnected from the receiving port, the transfer port is adapted for connection to a point-of-care testing device for transferring at least a portion of the multi-component blood sample from the cartridge to the point-of-care testing device. The cartridge may include an actuation member in fluid transfer communication with the transfer port. The actuation member is transitionable between an initial position in which the multi-component blood sample is stored within the cartridge and an activated position in which at least a portion of the multi-component blood sample is expelled from the transfer port.

The cartridge may further include a valve disposed in fluid communication with the transfer port. The valve being transitionable between a closed position in which the transfer port is sealed and an open position in which a portion of a multi-component blood sample is adapted to pass therethrough. In some configurations, the cartridge includes at least one resiliently deflectable arm releasably engagable with an interference engagement located within the receiving port of the housing for securing the cartridge to the housing. The cartridge may include electronic or machine readable information, such as a barcode.

In accordance with another embodiment of the present invention, a biological fluid collection device includes a housing having a receiving port and a puncturing element at least partially disposed within the housing. The puncturing element is moveable between a pre-actuated position, in which the puncturing element is retained within the housing and a puncturing position, in which at least a portion of the puncturing element extends through the housing. A cartridge is removably connectable to the receiving port of the housing. The cartridge defines a flow channel therein. The cartridge includes a port in fluid communication with the flow channel for intake and expulsion of a biological fluid sample. The flow channel includes a sample stabilizer disposed therein. The cartridge is adapted to receive a multi-component blood sample having a cellular portion and a plasma portion via the port. In one embodiment, the puncturing element may be part of a contact activated lancet device.

In one configuration the actuation member is in fluid transfer communication with the flow channel. The actuation member is transitionable between an initial position in which the multi-component blood sample is stored within the cartridge and an activated position in which at least a portion of the multi-component blood sample is expelled from the transfer port. In one embodiment, the actuation member is transitioned to the activated position only after a portion of the multi-component blood sample has mixed with the sample stabilizer. A separation member may be disposed at least partially within a portion of the flow channel. The separation member being configured to restrain the cellular portion and allow the plasma portion to pass therethrough. With the cartridge disconnected from the housing, the port is adapted for connection to a point-of-care testing device for closed transfer of at least a portion of the multi-component blood sample from the cartridge to the point-of-care testing device.

In one configuration, the cartridge flow channel includes a vent to atmosphere. The vent may include a porous membrane adapted to allow air to pass therethrough and retain the multi-component blood sample therein.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
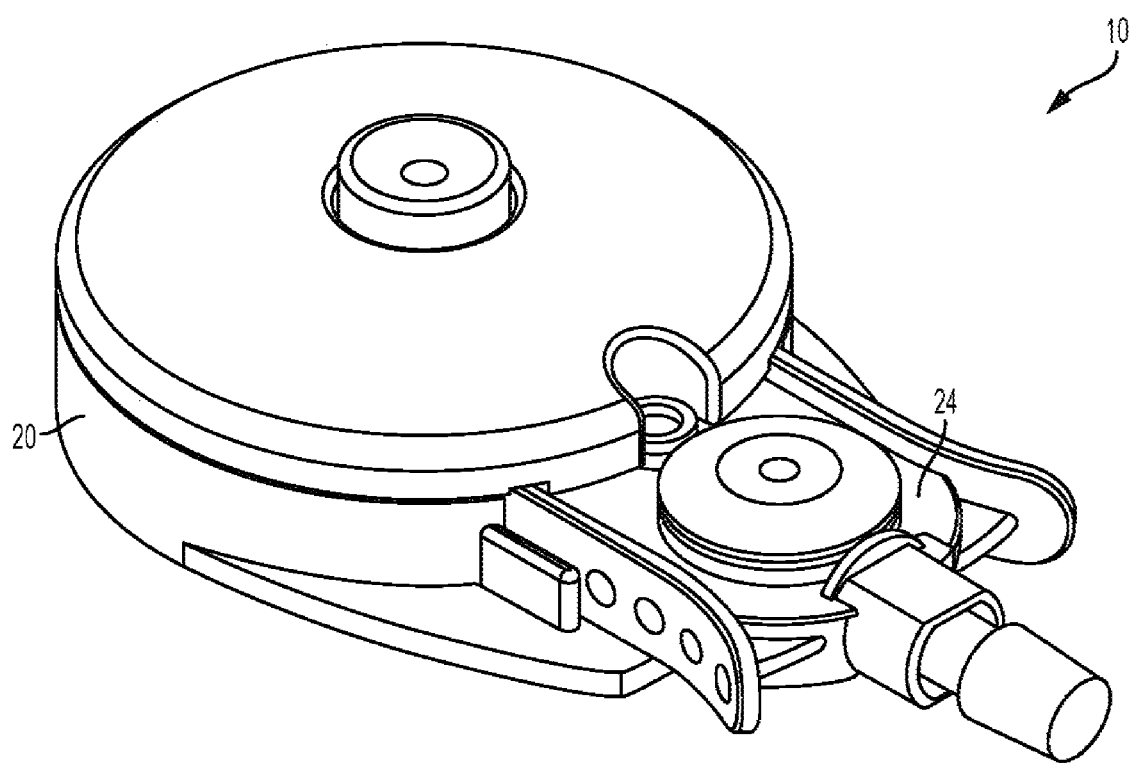
FIG. 1 is a perspective view of a biological fluid collection device in accordance with an embodiment of the present invention.
Figure 2:
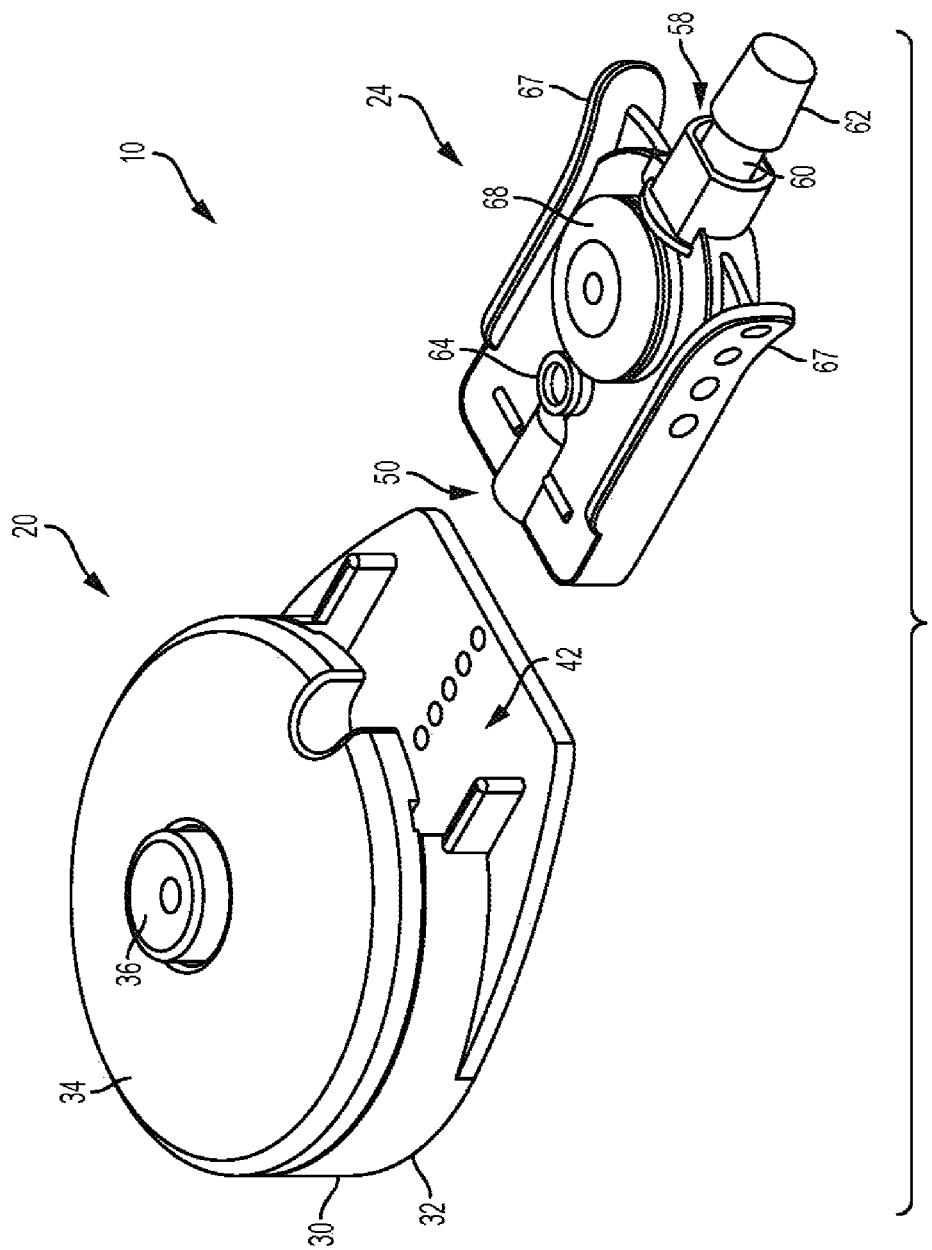
FIG. 2 is an exploded, perspective view of the biological fluid collection device of FIG. 1.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; 5) separating the sample at the point of collection; and 6) stabilizing the sample at the point of collection.

FIGS. 1-11 illustrate an exemplary embodiment of a biological fluid collection device of the present disclosure. Referring to FIGS. 1-11, 19, and 20, a biological fluid collection device 10 of the present disclosure is adapted to receive a multi-component blood sample 12 having a cellular portion 14 and a plasma portion 16. The biological fluid collection device 10 provides a closed system that reduces the exposure of a blood sample and provides fast mixing of a blood sample with a sample stabilizer.

The biological fluid collection device 10 generally includes a housing 20, a puncturing element 22, and a cartridge 24 removably connectable to a portion of the housing 20.

The housing 20 includes a sidewall 30, a bottom wall 32, a top wall 34, an actuation mechanism 36, an inlet port 38, a flow channel 40 defined within the housing 20 and in fluid communication with the inlet port 38, and a receiving port 42. In one embodiment, the actuation mechanism 36 is a push button. The sidewall 30, the bottom wall 32, and the top wall 34 of the housing 20 define an internal cavity 44 therein.

Figure 4:
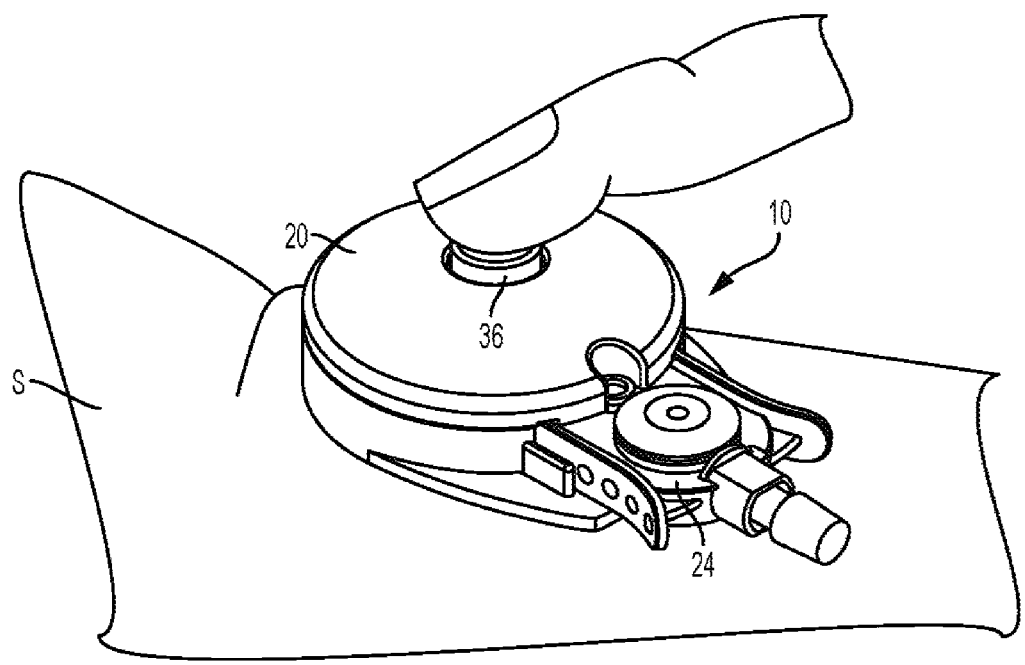
FIG. 4 is a perspective view of the biological fluid collection device of FIG. 1 in contact with a patient.
Figure 5:
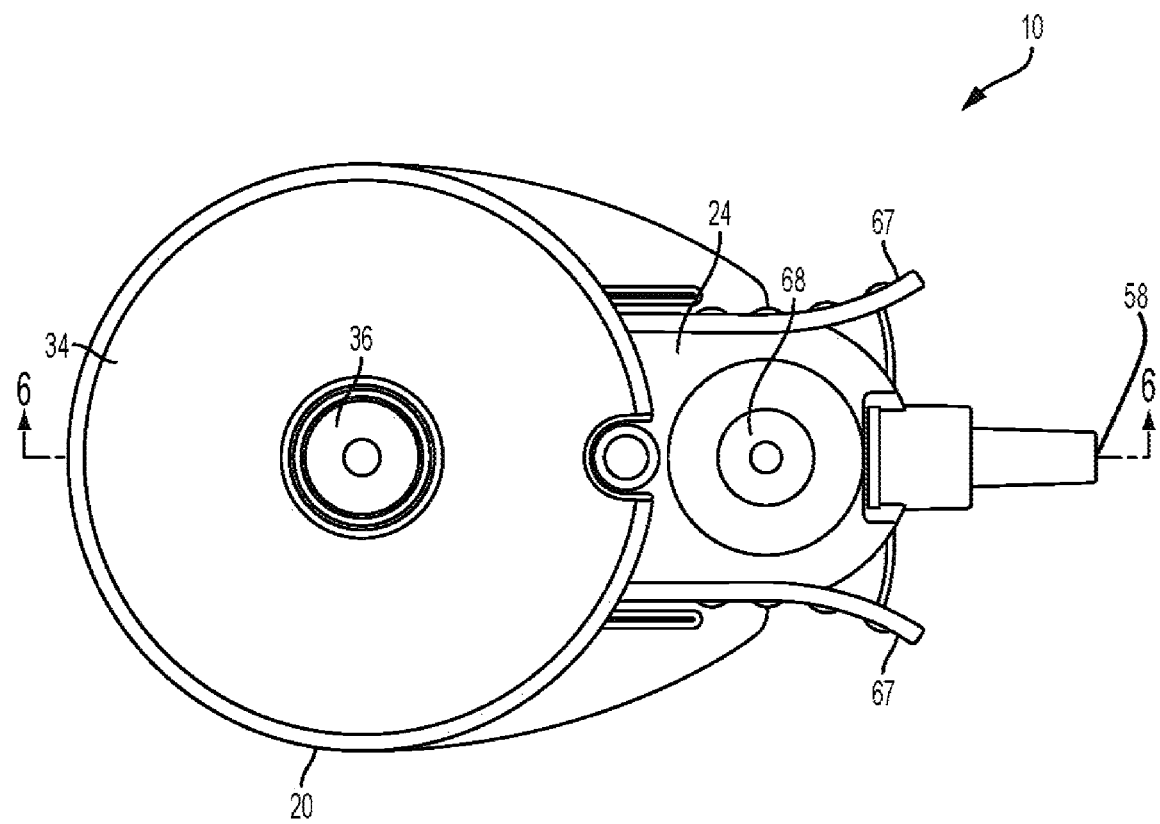
FIG. 5 is a top plan view of the biological fluid collection device of FIG. 1.
Figure 6:
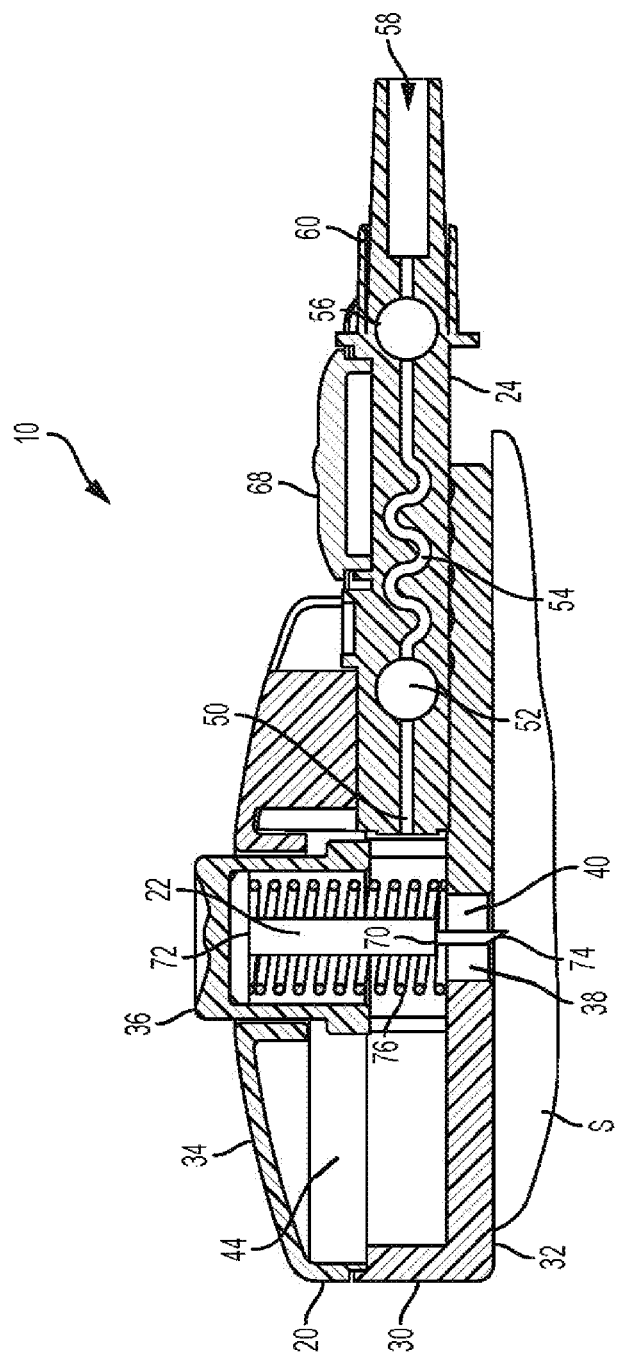
FIG. 6 is a cross-sectional view of the biological fluid collection device of FIG. 5, taken along line 6-6, of with a puncturing element in a puncturing position.
Figure 7:
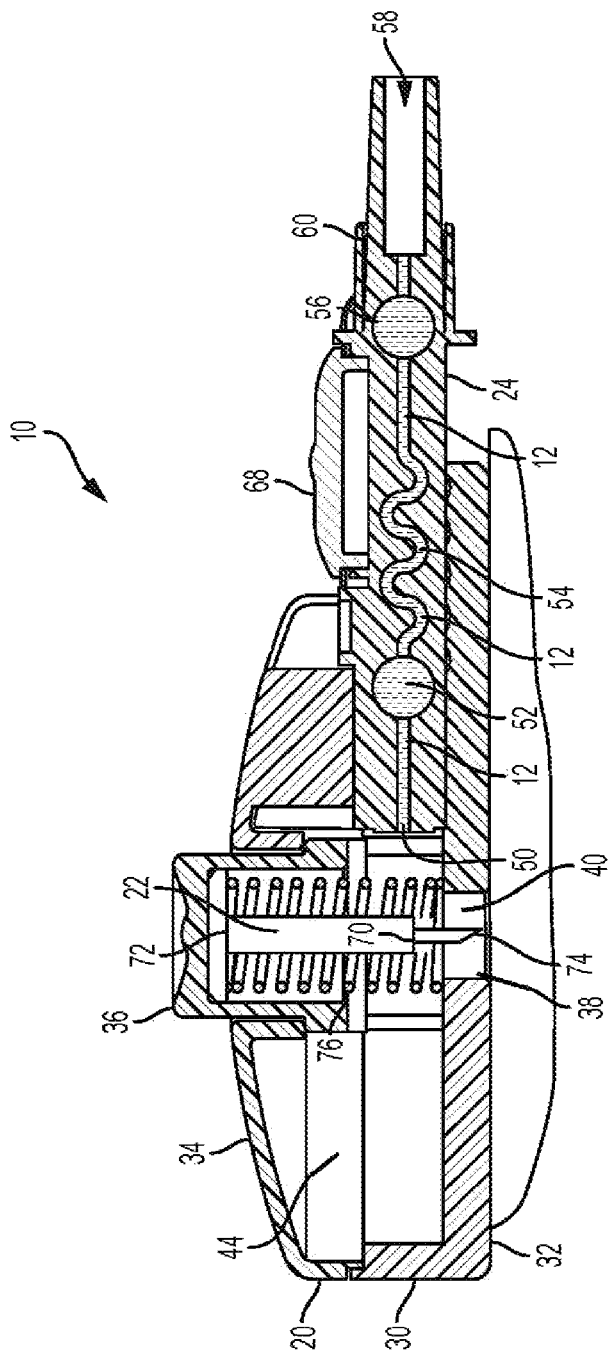
FIG. 7 is a cross-sectional view of the biological fluid collection device of FIG. 5, taken along line 6-6, with the puncturing element in a pre-actuated position.

The bottom wall 32 of the housing 20 may include a mechanism for removably adhering the biological fluid collection device 10 to a patient as shown in FIGS. 4, 6, and 7. For example, the bottom wall 32 of the housing 20 may include an adhesive so that the biological fluid collection device 10 can be secured onto a skin surface S of a patient where a blood sample will be accessed. In one embodiment, the adhesive of the bottom wall 32 is protected by a peel-off layer, similar to an adhesive bandage, which would be removed before placing the biological fluid collection device 10 on the skin surface S of the patient's body. A hydrogel or other layer (not shown) could be included to provide some thickness to the bottom wall 32 and help improve the stability of the adhesive seal. Additionally, the adhesive could include a chemistry to create a more liquid-tight seal, similar to painter's tape technology, where wetting from the paint itself causes a chemical reaction with the adhesive to create an improved water-tight barrier to prevent the paint from seeping under the tape. Importantly, the adhesive provides for proper adhesion of the bottom wall 32 of the biological fluid collection device 10 to the skin surface S of a patient and minimizes skin contact which leads to a better sample for coagulation testing. The adhesive of the bottom wall 32 can be punctured by the puncturing element 22 such that the blood evolving from the wound passes into the inlet port 38. In one embodiment, the bottom wall 32 includes two layers, a bottom portion having an adhesive layer that is in contact with the skin and an upper portion that receives the evolving blood. The adhesive of the present disclosure includes an anti-leak mechanism. For example, in one embodiment, a self-sealing or self-healing polymer is used. In another embodiment, the top wall 34 of the housing 20 comprises a dome-shaped wall, which compresses under the puncturing element 22, but which pops back to its original shape after a lancing action thereby providing a vacuum force that helps pull the blood out of the wound.

Figure 8:
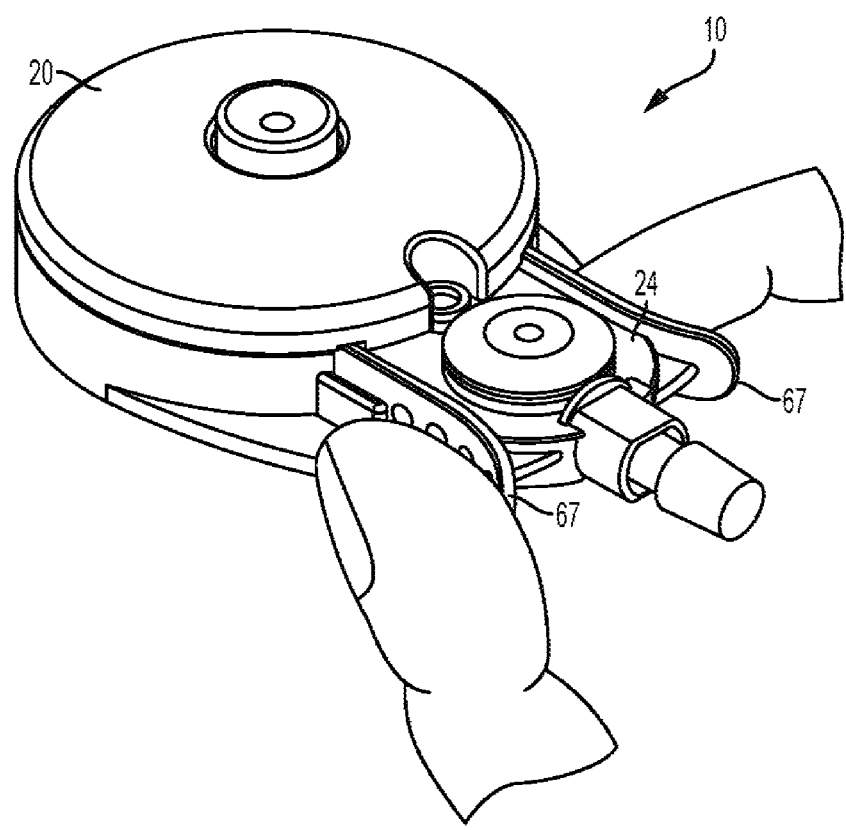
FIG. 8 is a perspective view of the biological fluid collection device of FIG. 1 with a user removing a cartridge from a housing in accordance with an embodiment of the present invention.
Figure 9:
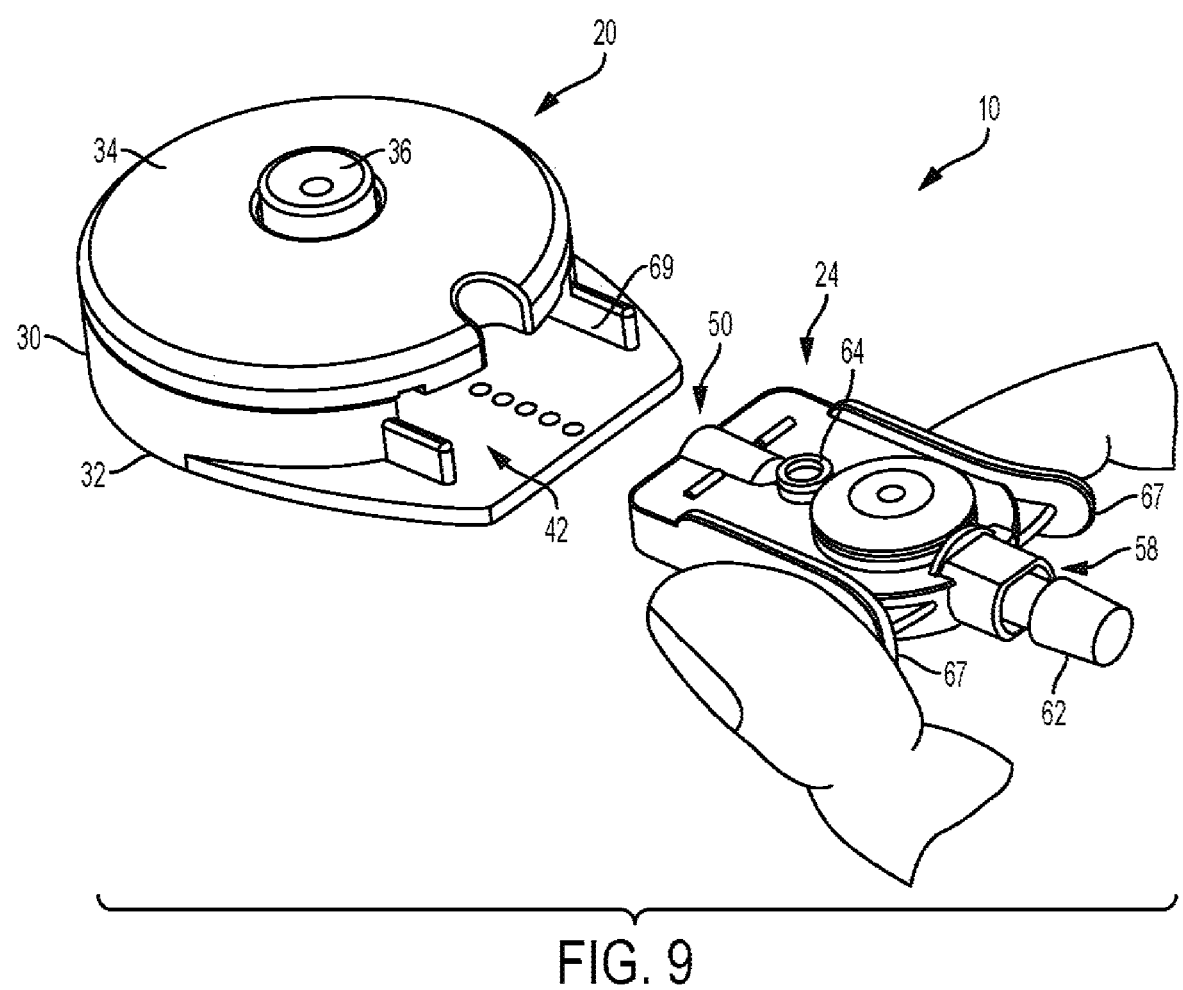
FIG. 9 is a perspective view of the biological fluid collection device of FIG. 8 after the user has removed the cartridge from the housing.

The cartridge 24 is removably connectable to a portion of the housing 20, such as the receiving port 42. The cartridge 24 includes an inlet port 50 in fluid communication with the inlet port 38 of the housing 20 via the flow channel 40, an entry reservoir 52 in fluid communication with the inlet port 50, a cartridge flow channel 54 defined within the cartridge 24 and in fluid communication with the entry reservoir 52, an exit reservoir 56 in fluid communication with the cartridge flow channel 54, an exit port or transfer port 58 in fluid communication with the exit reservoir 56, a valve 60 disposed in communication with the exit port 58, an end cap 62, a fill indicator 64, a readable information portion 66, arms 67, and a cartridge actuation member 68. In one embodiment, the end cap 62 is removably attachable to the cartridge 24 to seal the exit port 58. In one embodiment the arms 67 of the cartridge 24 are resiliently deflectable. Referring to FIGS. 8 and 9, the cartridge 24 can be removed from the housing 20 by squeezing the arms 67 to deflect the arms 67 out of engagement with an interference surface 69 disposed within the receiving port 42 of the housing 20.

In one embodiment, the fill indicator 64 comprises a transparent wall in a portion of the cartridge 24. In this manner, after a user has drawn a sufficient blood sample 12 into the cartridge 24 via the inlet port 38 of the housing 20, the fill indicator 64 turns red, thereby indicating that a portion of the entry reservoir 52, the cartridge flow channel 54, and/or the exit reservoir 56 adjacent the fill indicator 64 is full, thus, signaling to the user to stop drawing the blood sample 12.

Figure 3:
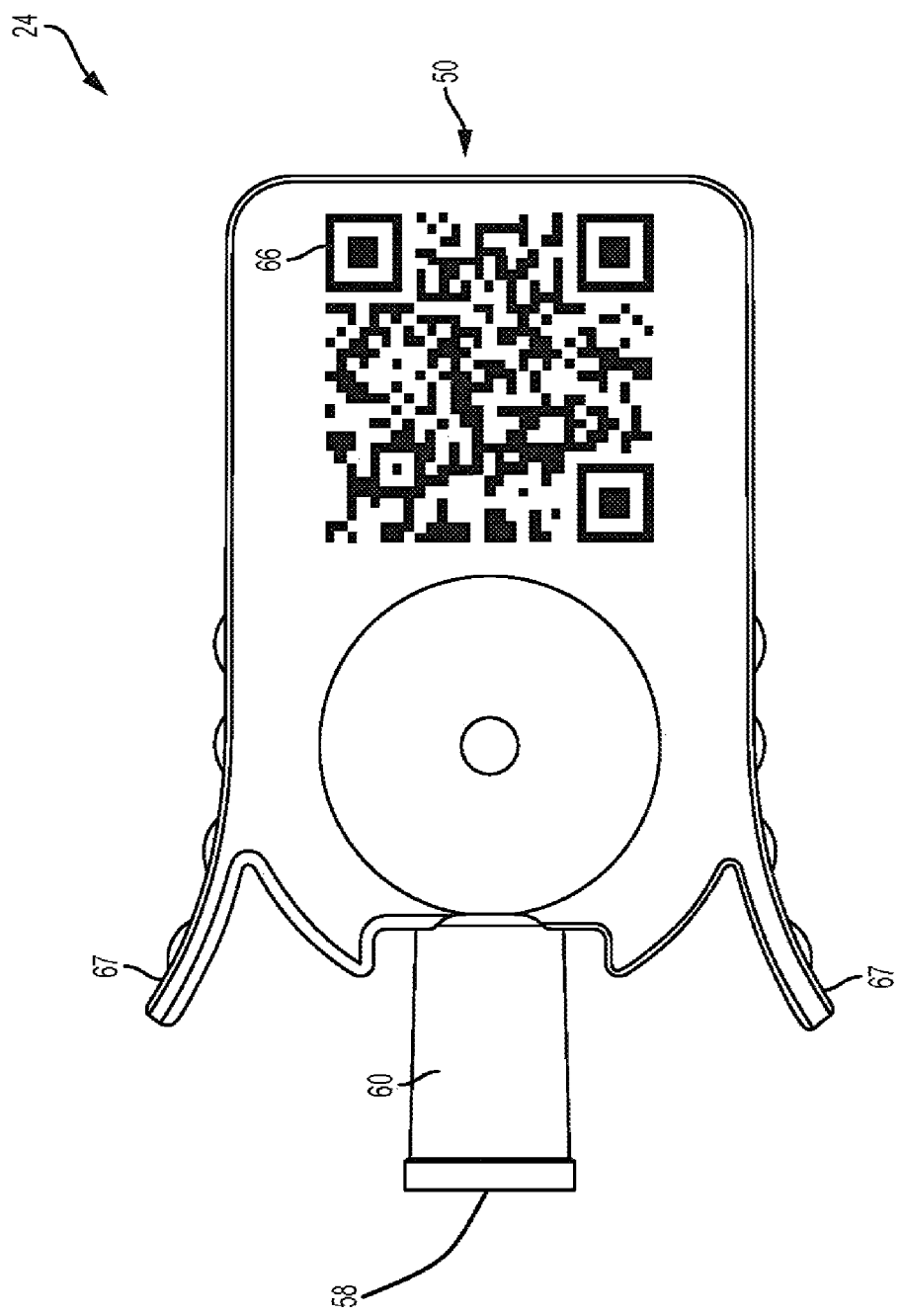
FIG. 3 is a top plan view of a cartridge with a readable information portion in accordance with an embodiment of the present invention.

In one embodiment, referring to FIG. 3, at least a part of the readable information 66 may include electronically readable information and/or machine readable information, a portion of which may be a barcode. For example, in one embodiment, included on a portion of the cartridge 24 is a barcode or some other machine readable data that is unique to each cartridge 24 or optionally unique to the contents of each cartridge 24. Such information may also be used for storage of additional data associated with a cartridge, such as cartridge manufacturer information, cartridge type, intended draw size information, and the like. In addition, patient-specific, test-specific, or other application-specific information may be stored, e.g., electronically, and associated with the cartridge's unique identifier.

In one embodiment, the cartridge flow channel 54 comprises a serpentine shape. In some embodiments, the cartridge flow channel 54 comprises a serpentine shape to promote efficient mixing of a blood sample 12 having a cellular portion 14 and a plasma portion 16. It is noted herein that the serpentine shape of the flow channel 54 may include undulations in the left and right, fore and aft, up and down, directions or any combinations thereof to promote efficient mixing of a blood sample 12.

Figure 11:
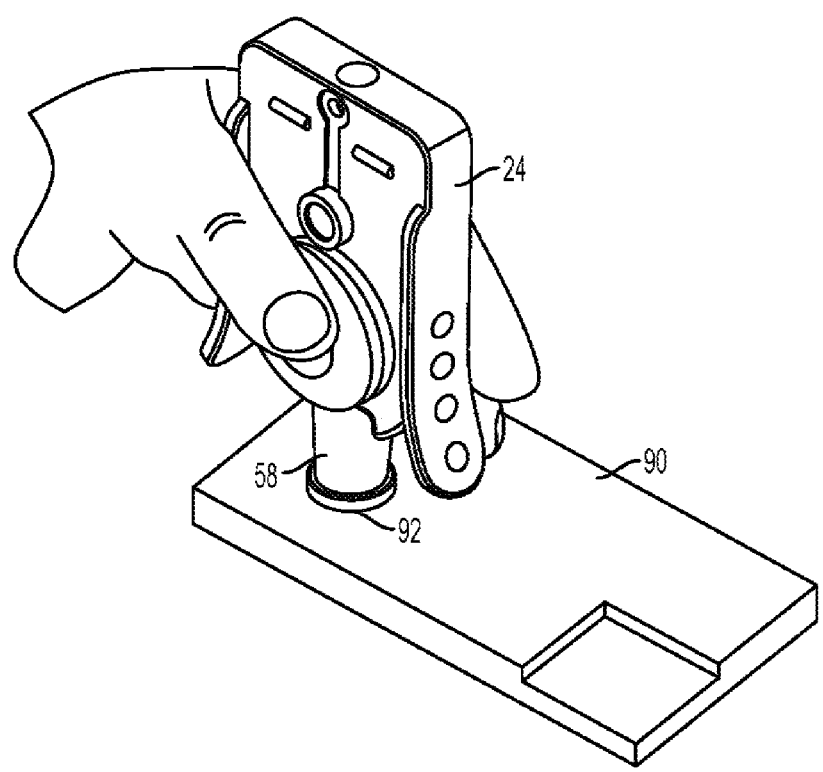
FIG. 11 is a perspective view of the cartridge of FIG. 8, engaged with a point-of-care testing device in accordance with an embodiment of the present invention.

The valve 60 is transitionable between a closed position to seal a blood sample 12 within the exit reservoir 56 of the cartridge 24 and an open position to allow a portion of the blood sample 12 to flow through the exit port 58 to a point-of-care testing device 90 as shown in FIG. 11. FIG. 11 is not drawn to scale. For example, the cartridge 24 of the present disclosure can be sized smaller in proportion to the size of a hand of a user. In FIG. 11, the cartridge 24 is illustrated larger in scale for clarity purposes only.

Referring to FIGS. 1 and 4-7, with the cartridge 24 connected to the housing 20, the cartridge flow channel 54 is in fluid communication with the inlet port 38 of the housing 20 via the flow channel 40.

With the cartridge 24 disconnected from the housing 20, the cartridge flow channel 54 is sealed. In some embodiments, the cartridge 24 is removably connected to the housing 20 via a frangible element or frangible portion (not shown). The frangible element includes a frangible element sealing wall. In this manner, after the frangible element is broken to remove the cartridge 24 from the housing 20, the frangible element sealing wall is configured to seal the inlet port 50 of the cartridge 24. In other configurations, the cartridge 24 may be engaged with the housing 20 through a mechanical interlock.

The cartridge actuation member 68 is in communication with the exit port. The actuation member 68 is transitionable between an initial position in which the multi-component blood sample 12 is storable within the cartridge 24 and an activated position in which the multi-component blood sample 12 is expelled from the exit port 58.

The puncturing element 22 is at least partially disposed within the housing 20 and is transitionable between a pre-actuated position (FIG. 7) wherein the puncturing element 22 is retained within the housing 20 and a puncturing position (FIG. 6) wherein at least a portion of the puncturing element 22 extends through the inlet port 38 of the housing 20 establishing fluid communication with the flow channel 40. In one embodiment, the housing 20 and the puncturing element 22 are part of a lancet microarray device.

Referring to FIGS. 6 and 7, the puncturing element 22 includes a forward end 70, a backward end 72, a puncturing end 74 at the forward end 70 of the puncturing element 22, and a spring 76.

The puncturing element 22 is adapted for axial or longitudinal movement through the internal cavity 44 of the housing 20 between an initial armed or pre-actuated position (FIG. 7) with the puncturing end 74 maintained within the housing 20 to a puncturing position (FIG. 6) in which the puncturing end 74 extends through the inlet port 38 of the housing 20. Puncturing end 74 is adapted for puncturing the skin surface S of a patient, and may define a pointed end, a blade edge, and the like. Puncturing end 74 may include a preferred alignment orientation, such as with a pointed end of a blade aligned in a specific orientation.

Referring to FIGS. 6 and 7, the spring 76 may be provided around the puncturing element 22 for retracting the puncturing end 74 within the housing 20 after the puncturing end 74 is axially moved to the puncturing position. The spring 76 extends between a surface of the bottom wall 32 of the housing 20 and the actuation mechanism 36. The spring 76 is typically a compression spring, capable of storing energy when in a compressed state.

A user or an operator may actuate or activate the actuation mechanism 36 of the housing 20 to move the puncturing element 22 from the pre-actuation position (FIG. 7) to the puncturing position (FIG. 6) thereby causing the lancing of the skin surface S of the patient by the puncturing end 74 as shown in FIG. 6. When the actuation mechanism 36 of the housing 20 is depressed, the puncturing end 74 cuts into the skin surface S of the patient's body and capillary blood begins to flow into the inlet port 38 of the housing 20. In one embodiment, a wicking element may surround the inlet port 38, creating a chamber to pool the blood and by a wicking motion collect the blood, pulling it into the housing 20.

In one embodiment, the biological fluid collection device 10 of the present disclosure provides a closed sampling and transfer system that reduces the exposure of a blood sample and provides fast mixing of a blood sample with a sample stabilizer 80.

Figure 19:
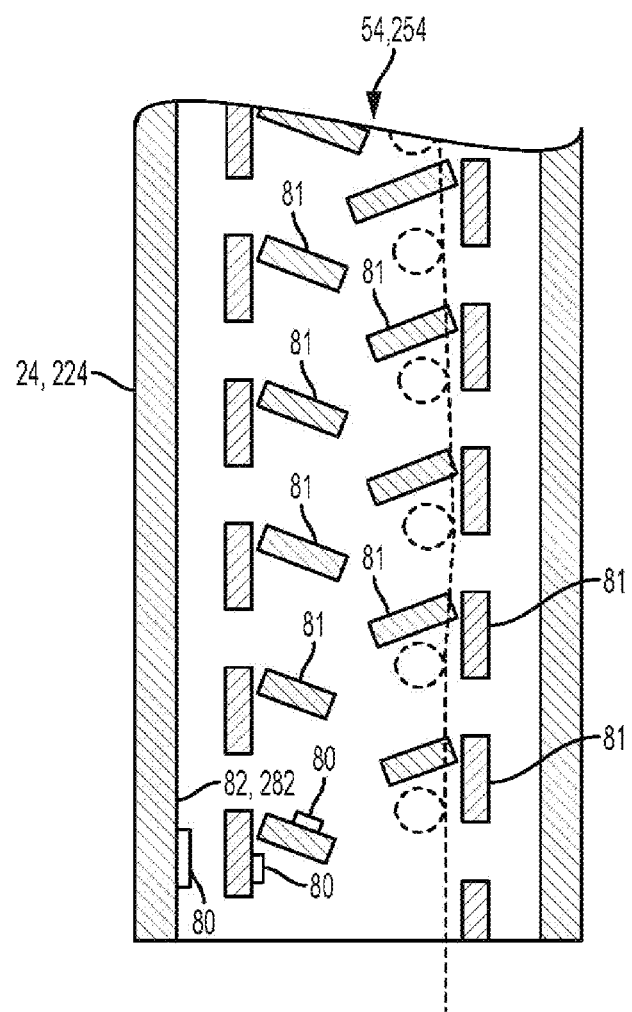
FIG. 19 is a cross-sectional view of a flow channel of a biological fluid collection device in accordance with an embodiment of the present invention.

For example, referring to FIG. 19, the cartridge 24 is adapted to contain a sample stabilizer 80 to provide passive and fast mixing of a blood sample 12 with the sample stabilizer 80. The sample stabilizer 80, can be an anticoagulant, or a substance designed to preserve a specific element within the blood such as, for example, RNA, protein analyte, or other element. In one embodiment, the sample stabilizer 80 is heparin or EDTA. In one embodiment, a plurality of biological fluid collection devices 10 could include different sample stabilizers. A biological fluid collection device 10 of the present disclosure provides flexibility in the nature of the additives and/or sample stabilizers introduced for a blood sample.

In one embodiment, the sample stabilizer 80 is provided within a portion of the cartridge flow channel 54. In other embodiments, the sample stabilizer 80 is provided in other areas of the biological fluid collection device 10 such as the housing 20.

In one embodiment, the biological fluid collection device 10 includes a sample stabilizer 80 disposed within a portion of the cartridge flow channel 54. In one embodiment, the flow channel 54 may also include agitation members 81. The agitation members 81 can control a flow pattern of the blood sample 12 to induce mixing of the blood sample 12 and the sample stabilizer 80. In one embodiment, the agitation members 81 can be in the form of a flute or rib that is co-molded with the flow channel 54 and the sample stabilizer 80 can be coated on the flutes and/or on an inner sidewall surface 82 of the flow channel 54.

In one embodiment, the biological fluid collection device 10 of the present disclosure is adapted to receive a blood sample 12 having a cellular portion 14 and a plasma portion 16. After collecting the blood sample 12, the biological fluid collection device 10 is able to separate the plasma portion 16 from the cellular portion 14. After separation, the biological fluid collection device 10 is able to transfer the plasma portion 16 of the blood sample 12 to a point-of-care testing device.

Figure 20:
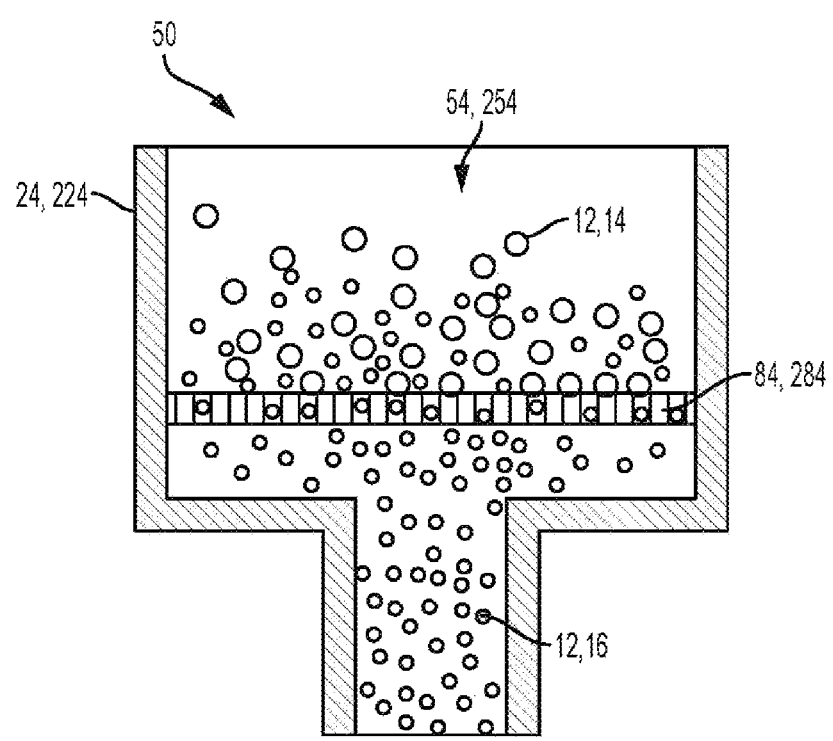
FIG. 20 is a schematic representation of a separation member of a biological fluid collection device in accordance with an embodiment of the present invention.

Referring to FIG. 20, in one embodiment, the biological fluid collection device 10 includes a blood separation element or separation member 84 disposed at least partially within a portion of the cartridge flow channel 54 between the inlet port 50 and the exit port 58. The blood separation element 84 is adapted to trap the cellular portion 14 of the blood sample 12 within the flow channel 54 and allow the plasma portion 16 of the blood sample 12 to pass through the blood separation element 84 to the exit port 58 as shown in FIG. 20.

In one embodiment, the blood separation element 84 is disposed within a portion of the flow channel 54 and the blood separation element 84 is adapted to restrain a cellular portion 14 of the multi-component blood sample 12 and to allow a plasma portion 16 of the multi-component blood sample 12 to pass therethrough.

In one embodiment, the blood separation element 84 may be either hollow fiber membrane filters commercially available, or flat membrane filters, such as track-etch filters commercially available. Membrane filter pore size and porosity can be chosen to optimize separation of clean (i.e., red blood cell free, white blood cell free, and platelet free) plasma in an efficient manner. In another embodiment, the blood separation element 84 includes a lateral flow membrane. In other embodiments, the blood separation element 84 may comprise any filter that is able to trap the cellular portion 14 of the blood sample 12 within the flow channel 54 and allow the plasma portion 16 of the blood sample 12 to pass through the blood separation element 84 to the exit port 58.

Referring to FIG. 11, with the cartridge 24 disconnected from the housing 20, the exit port 58 is adapted for connection to a point-of-care testing device 90 for closed transfer of at least a portion of the multi-component blood sample 12 from the cartridge 24 to the point-of-care testing device 90.

Referring again to FIGS. 1-11, use of a biological fluid collection device 10 of the present disclosure will now be described. Referring to FIG. 4, upon selecting a site, a user, an operator, or a clinician may adhere the biological fluid collection device 10 over a selected sampling site.

A user may then actuate or activate the actuation mechanism 36 of the housing 20 to move the puncturing element 22 from the pre-actuation position (FIG. 7) to the puncturing position (FIG. 6) thereby causing the lancing of the skin surface S of the patient by the puncturing end 74 as shown in FIG. 6. When the actuation mechanism 36 of the housing 20 is depressed, the puncturing end 74 cuts into the skin surface S of the patient's body and capillary blood begins to flow into the inlet port 38 of the housing 20.

Referring to FIGS. 8 and 9, when the cartridge 24 is filled with a blood sample 12, the clinician can remove the cartridge 24 from the housing 20. When removed from the housing 20, the flow channel 54 of the cartridge 24 is sealed from the external environment.

In some embodiments, the cartridge 24 of the biological fluid collection device 10 can be used to separate the plasma portion 16 from the cellular portion 14 of the blood sample 12 using the blood separation element 84 and the blood sample 12 can be mixed with a sample stabilizer 80 as described above.

Figure 10:
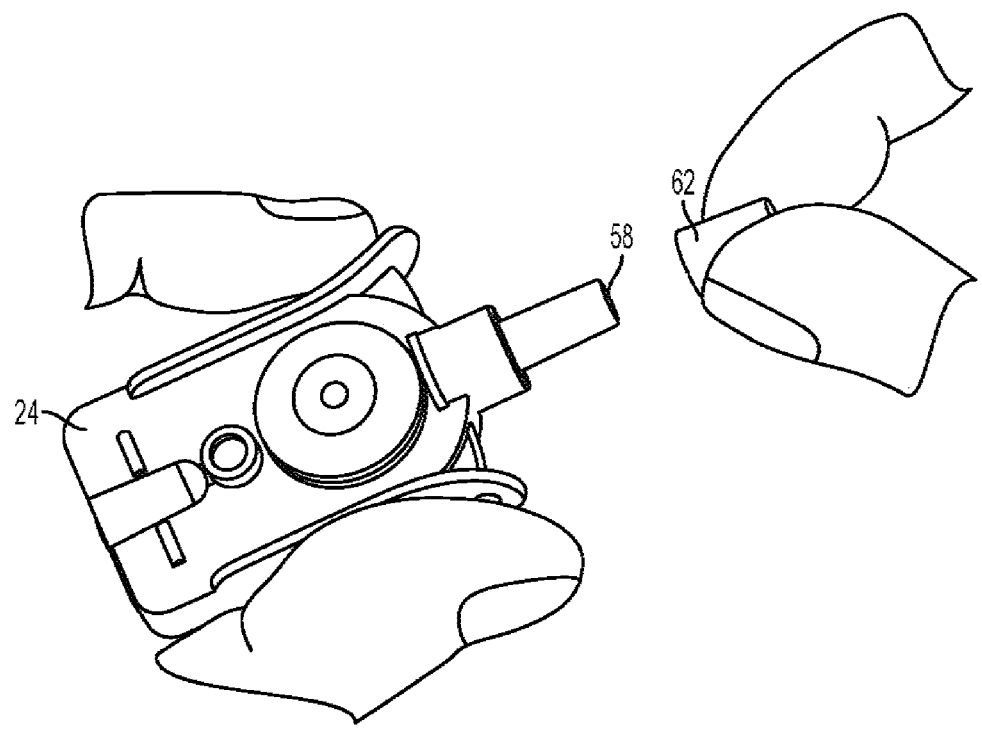
FIG. 10 is a perspective view of the cartridge of FIG. 8 with a user removing a cap from the cartridge in accordance with an embodiment of the present invention.

Referring to FIGS. 10 and 11, after the blood sample 12 is stabilized and separated, a user may remove the end cap 62 from the cartridge 24 and the cartridge 24 may be engaged with a blood testing device or point-of-care testing device 90 for closed transfer of a portion of the homogenously stabilized blood sample from the biological fluid collection device 10 to the blood testing device or point-of-care testing device 90. The blood testing device 90 is adapted to receive the homogenously stabilized blood sample to analyze the homogenously stabilized blood sample and obtain test results.

With the cartridge 24 engaged with a blood testing device 90, a user may depress the cartridge actuation member 68 to move the cartridge actuation member 68 to an activated position in which the multi-component blood sample 12 is expelled from the exit port 58 to the blood testing device 90.

In one embodiment, referring to FIG. 11, the exit port 58 of the cartridge 24 may be engaged with a point-of-care testing device 90. For example, the exit port 58 may be placed over a receiving port 92 of the point-of-care testing device 90 as shown in FIG. 11. Next, a clinician may transfer a portion of a blood sample 12, e.g., a plasma portion 16 of the blood sample 12, to the point-of-care testing device 90 in a closed manner, reducing exposure to the clinician and the patient. The point-of-care testing device 90 is adapted to receive the exit port 58 of the cartridge 24 for closed transfer of a portion of the plasma portion 16 of the blood sample 12 from the cartridge 24 to the point-of-care testing device 90. The point-of-care testing device 90 is adapted to receive the plasma portion 16 to analyze the blood sample and obtain test results.

Figure 12:
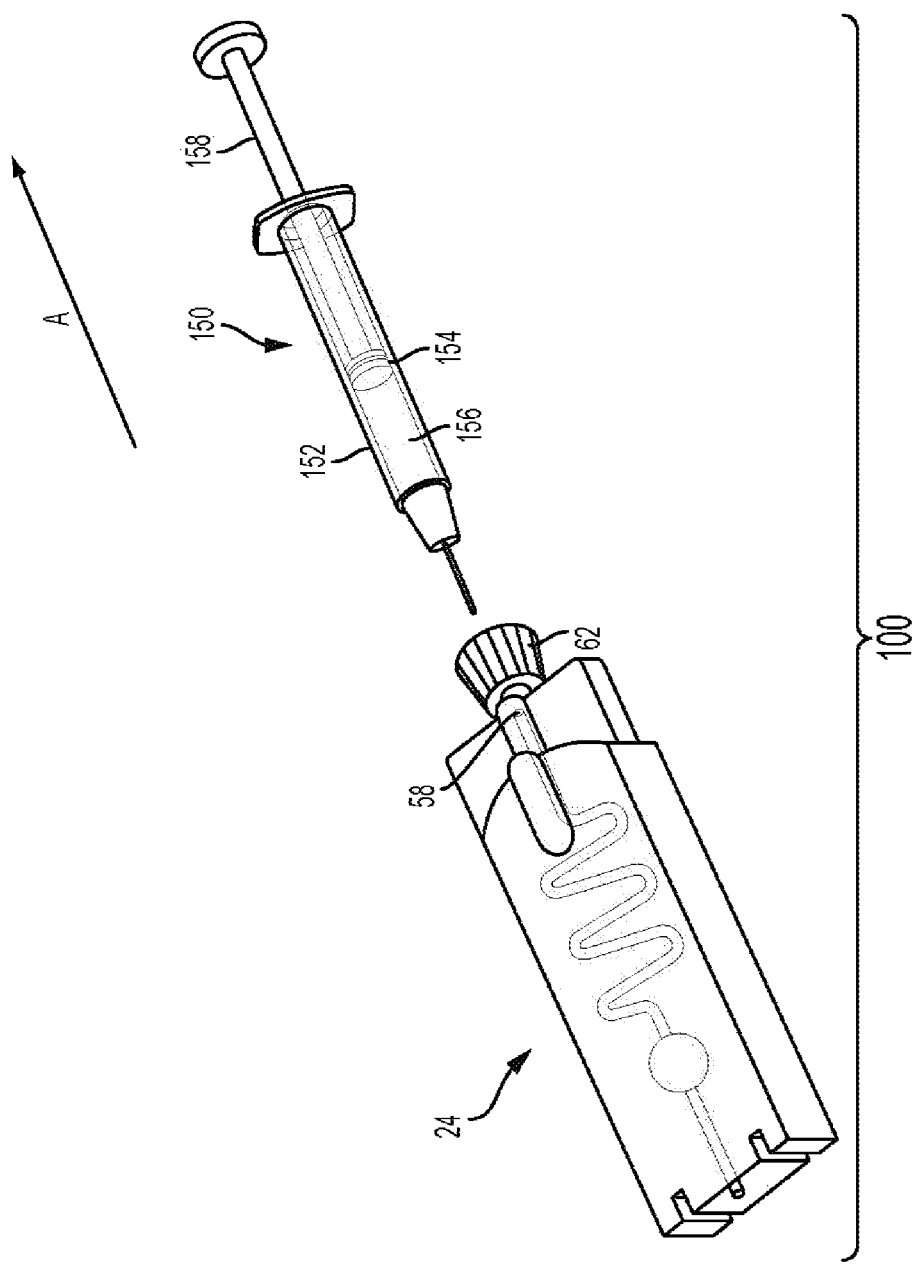
FIG. 12 is a perspective view of a cartridge and a syringe assembly in accordance with another embodiment of the present invention.
Figure 13:
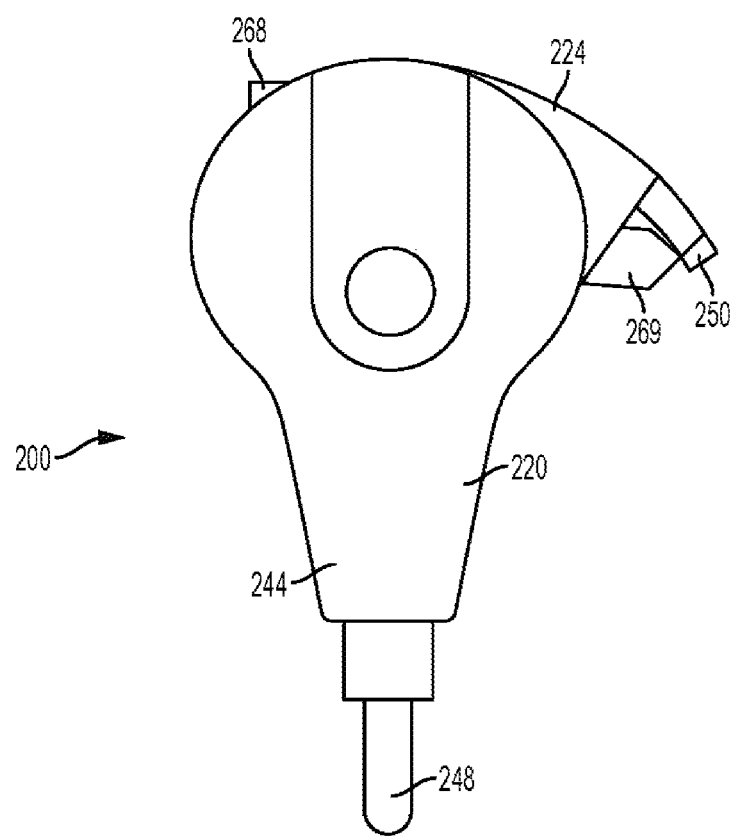
FIG. 13 is a top plan view of a biological fluid collection device in accordance with another embodiment of the present invention.
Figure 14:
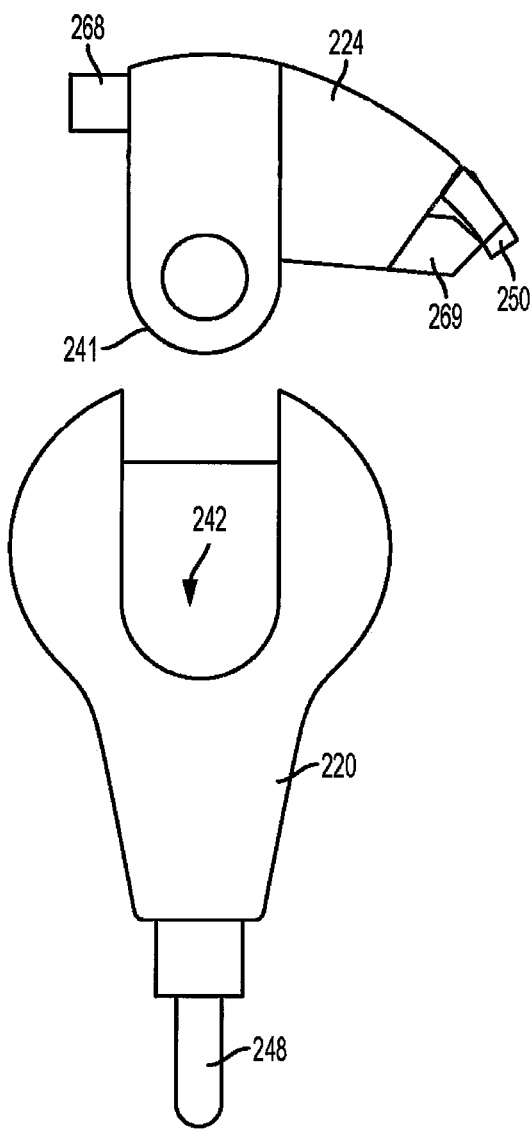
FIG. 14 is a top plan view of the biological fluid collection device of FIG. 13 having a cartridge removed from a housing.

FIG. 12 illustrates another exemplary embodiment and includes similar components to the embodiment illustrated in FIGS. 1-11. For the sake of brevity, these similar components and the similar steps of using biological fluid collection device 100 will not all be discussed in conjunction with FIG. 12.

The biological fluid collection device 100 may include a syringe 150 that is connectable to an exit port 58 and/or an end cap 62 of the cartridge 24 of the biological fluid collection device 100. The syringe 150 includes a syringe barrel 152, a stopper 154 slideably disposed within an interior 156 of the syringe barrel 152, and a plunger rod 158 connected to the stopper 154. The plunger rod 158 is moveable with respect to the syringe barrel 152 to alter the position of the stopper 154 within the syringe barrel 152.

For example, with the syringe 150 connected to the cartridge 24, retraction of the plunger rod 158 with respect to the syringe barrel 152 in a direction generally along arrow A (FIG. 12) draws a multi-component blood sample 12 within the cartridge 24 through a separation member 84 (FIG. 20) within the cartridge 24. In one embodiment, the blood separation element 84 is disposed within a portion of the cartridge 24 and the blood separation element 84 is adapted to restrain a cellular portion 14 of the multi-component blood sample 12 and to allow a plasma portion 16 of the multi-component blood sample 12 to pass therethrough.

FIGS. 13-18, 21, and 22 illustrate another exemplary embodiment of a biological fluid collection device of the present disclosure. Referring to FIGS. 13-22, a biological fluid collection device 200 of the present disclosure is adapted to receive a multi-component blood sample 12 having a cellular portion 14 and a plasma portion 16. The biological fluid collection device 200 provides a closed system that reduces the exposure of a blood sample and provides fast mixing of a blood sample with a sample stabilizer.

The biological fluid collection device 200 generally includes a housing 220, a puncturing element 222, and a cartridge 224 removably connectable to a portion of the housing 220. The housing 220 defines a receiving port 242 adapted to receive the cartridge 224 and an internal cavity 244 in which the puncturing element 222 is disposed. The puncturing element 222 includes a puncturing end 274.

Figure 21:
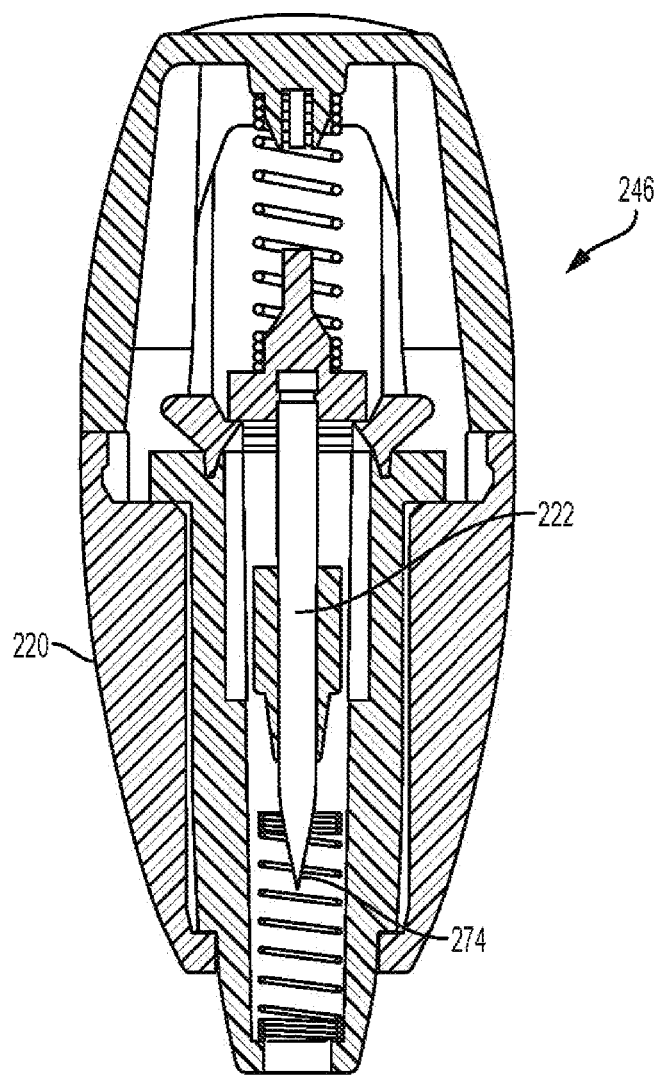
FIG. 21 is a cross-sectional view of a puncturing element of a housing of a biological fluid collection device, with the puncturing element in a pre-actuated position, in accordance with an embodiment of the present invention.
Figure 22:
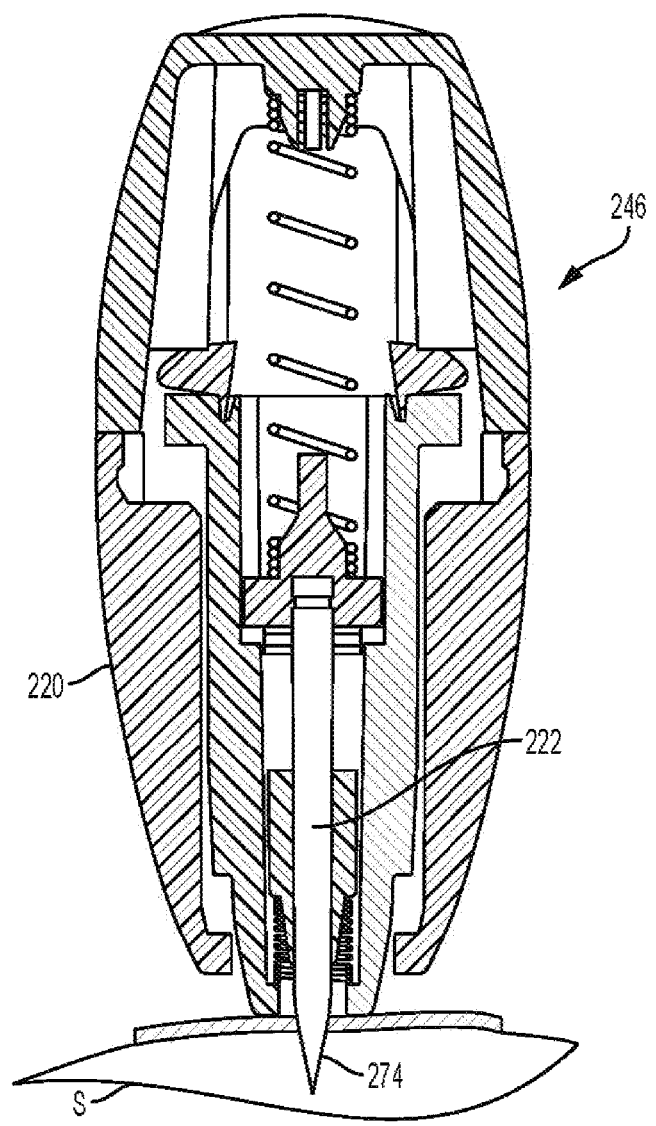
FIG. 22 is a cross-sectional view of a puncturing element of a housing of a biological fluid collection device, with the puncturing element in a puncturing position, in accordance with an embodiment of the present invention.

Referring to FIGS. 21 and 22, in one embodiment, the housing 220 and the puncturing element 222 are part of a contact activated lancet device 246. The puncturing element 222 is moveable between a pre-actuated position (FIG. 21) wherein the puncturing element 222 is retained within the housing 220 and a puncturing position (FIG. 22) wherein at least a portion of the puncturing element 222 extends through the housing 220.

The puncturing element 222 is adapted for axial or longitudinal movement through the internal cavity 244 of the housing 220 between an initial armed or pre-actuated position (FIG. 21) with the puncturing end 274 maintained within the housing 220 to a puncturing position (FIG. 22) in which the puncturing end 274 extends through the housing 220. Puncturing end 274 is adapted for puncturing the skin surface S of a patient, and may define a pointed end, a blade edge, and the like. Puncturing end 274 may include a preferred alignment orientation, such as with a pointed end of a blade aligned in a specific orientation.

In one embodiment, the biological fluid collection device 200 includes a tab member 248 removably securable to a portion of the housing 220 to enclose and shield the puncturing element 222.

Referring to FIGS. 13-18, the cartridge 224 is removably connectable to a portion of the housing 220 and defines a cartridge flow channel 254 therein. The cartridge 224 includes a port 250. The cartridge flow channel 254 is in fluid communication with the port 250. In one embodiment, a connecting portion 241 of the cartridge 224 is removably connectable to the receiving port 242 of the housing 220 via a snap fit connection. In one embodiment, the cartridge flow channel 254 includes a vent 269 to atmosphere. The cartridge 224 is adapted to receive a multi-component blood sample 12 having a cellular portion 14 and a plasma portion 16 via the port 250.

Figure 16:
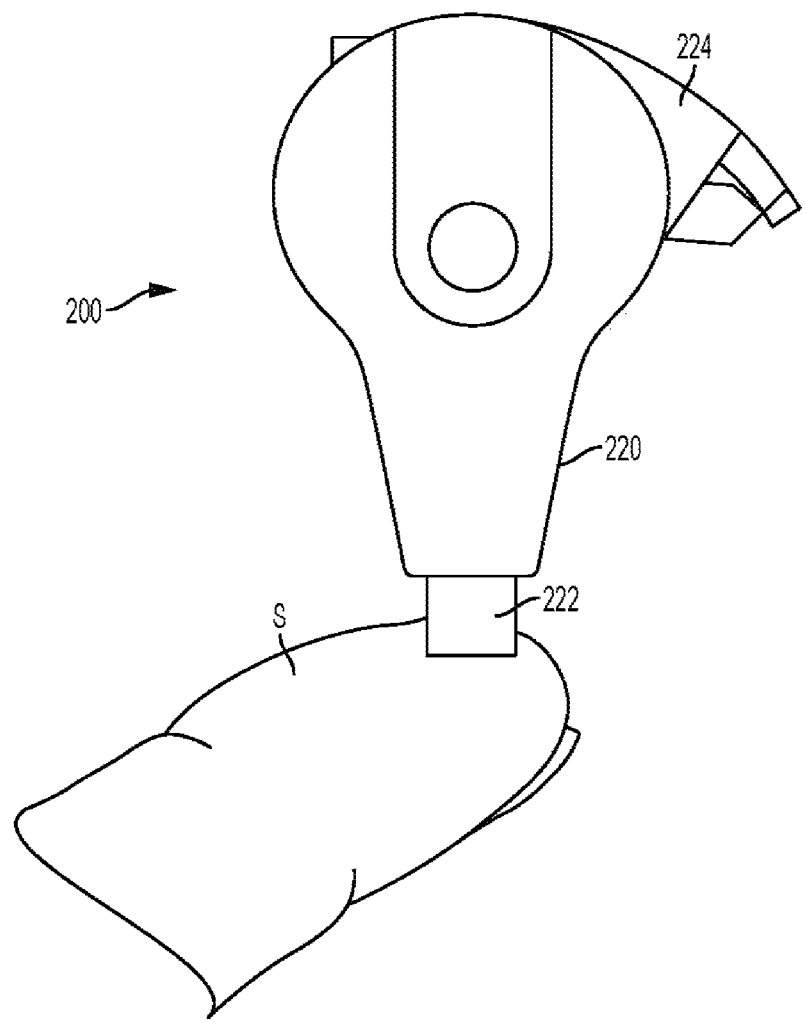
FIG. 16 is top plan view of the biological fluid collection device of FIG. 13 with a first portion of the device being in contact with a patient.

As shown in FIG. 16, after the puncturing element 222 pierces the skin S of the patient, the port 250 of the cartridge 224 includes a vented portion that pulls off a first drop of blood. In one embodiment, the port 250 of the cartridge 224 includes a vent or a vent hole. In another embodiment, the port 250 of the cartridge 224 contains a small sponge or a wicking material that assists in drawing a first drop of blood. In other embodiments, the port 250 of the cartridge 224 may include any mechanism that is adapted to pull a first drop of blood into the cartridge flow channel 254.

Figure 15:
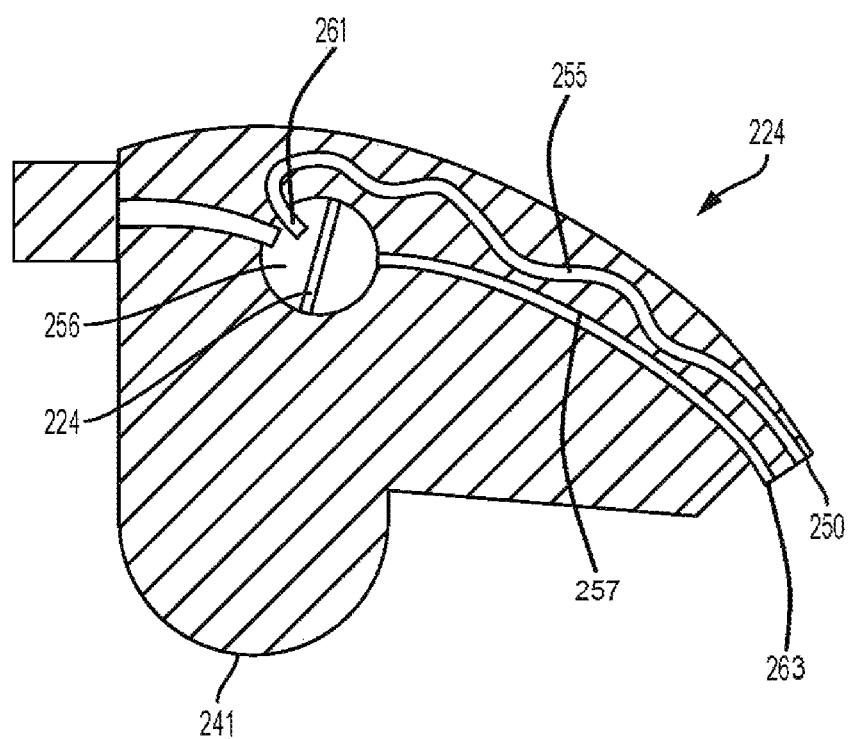
FIG. 15 is a cross-sectional view of the cartridge of the biological fluid collection device of FIG. 14.
Figure 17:
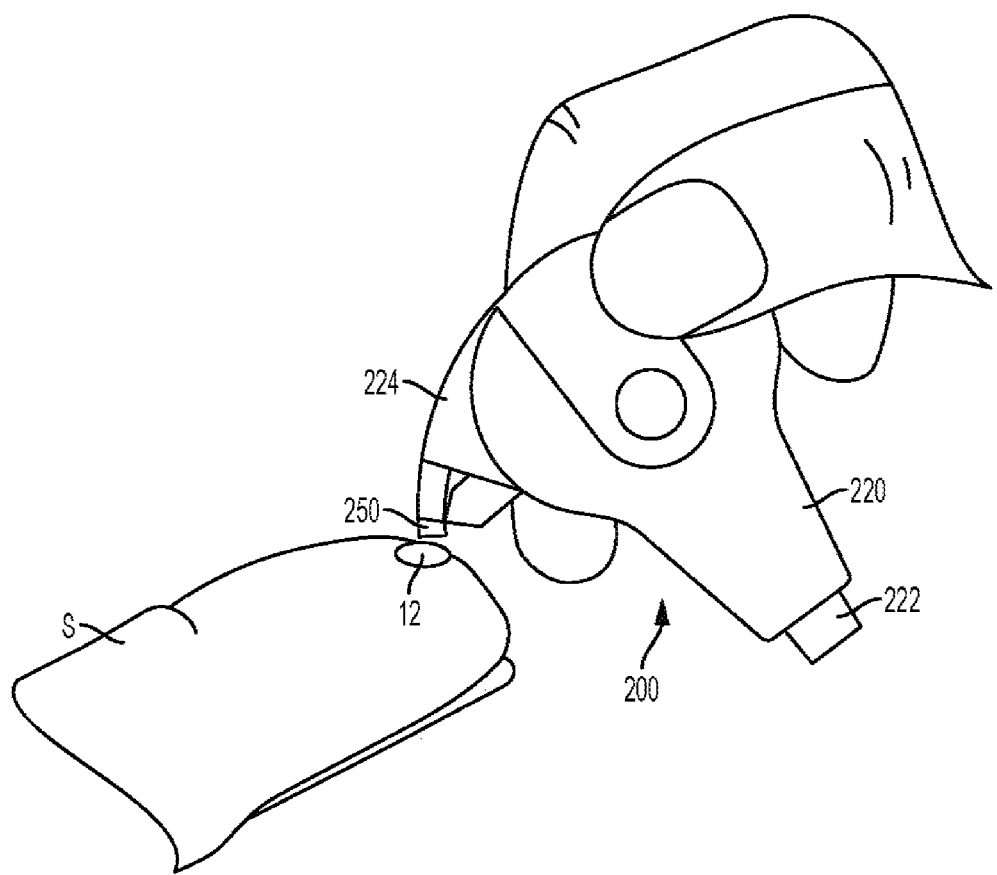
FIG. 17 is a perspective view of the biological fluid collection device of FIG. 13 with a second portion of the device being in contact with a patient.

As shown in FIG. 17, the cartridge 224 also includes an actuation member 268 in fluid communication with the port 250. Referring to FIG. 15, the cartridge flow channel 254 may generally be serpentine shaped including undulations in the left and right, fore and aft, up and down, directions or any combinations thereof to promote efficient mixing of a blood sample 12. The flow channel 254 may comprise a reservoir 256 for storing the multi-component blood sample 12 therein. In one particular embodiment, the flow channel 254 includes an inlet flow channel 255 extending between the port 250 and the reservoir 256 and an outlet flow channel 257 extending between the reservoir and the port 250. A one-way valve 261 is disposed between the inlet flow channel 255 and the reservoir 256 to prevent the multi-component blood sample 12 from flowing back into the inlet flow channel 255 after entering the reservoir 256. A one-way valve 263 may also be disposed within the outlet flow channel 257 adjacent the port 250 to prevent the multi-component blood sample 12 from entering the cartridge 224 via the outlet port 257.

The actuation member 268 of the cartridge 224 is transitionable between an initial position in which a multi-component blood sample 12 is storable within the cartridge 224 and an activated position in which the multi-component blood sample 12 is expelled from the port 250. In one embodiment, the actuation member 268 is a plunger.

In one embodiment, the port 250 and/or the cartridge flow channel 254 of the cartridge 224 includes a porous membrane adapted to allow air to escape and retain the multi-component blood sample 12 within the cartridge flow channel 254. In this manner, once a blood sample 12 is received within the cartridge flow channel 254 of the cartridge 224, the blood sample 12 must be forced out the cartridge 224 to expel the blood sample 12 from the cartridge 224. For example, in one embodiment, the actuation member 268 is used to force the blood sample 12 out the cartridge 224 by transitioning the actuation member 268 to the activated position, e.g., by depressing the actuation member 268 as shown in FIG. 18.

Figure 18:
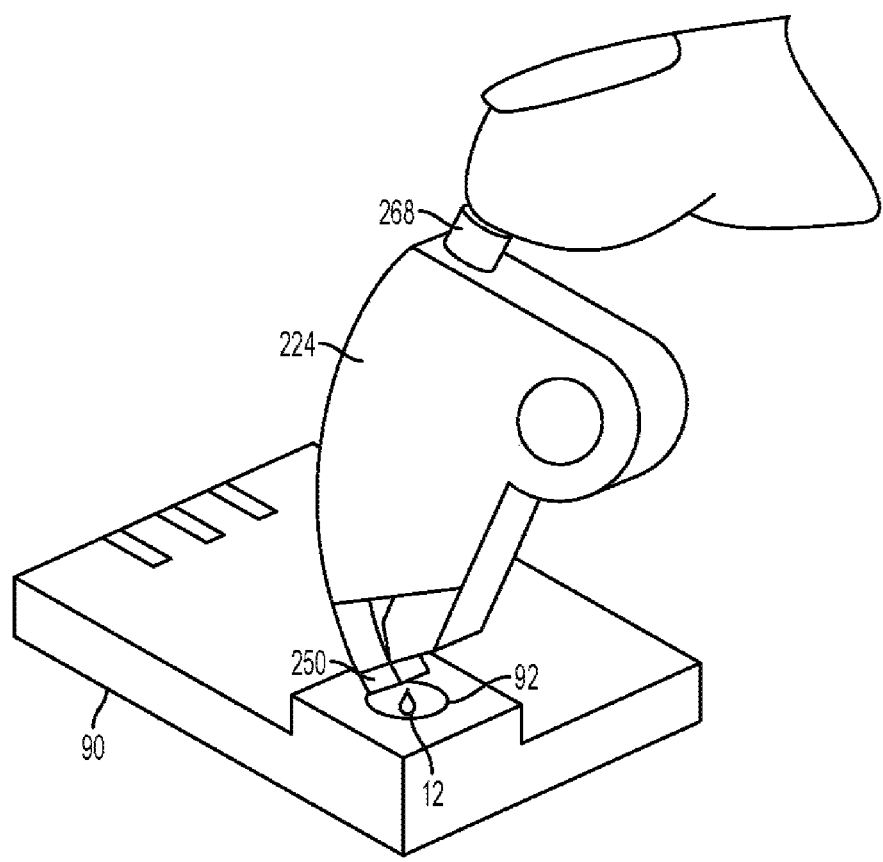
FIG. 18 is a perspective view of the cartridge of the biological fluid collection device of FIG. 13 and a point-of-care testing device in accordance with another embodiment of the present invention.

With continued reference to FIG. 18, the biological fluid collection device 200 of the present disclosure provides a closed sampling and transfer system that reduces the exposure of a blood sample and provides fast mixing of a blood sample with a sample stabilizer 80.

For example, the cartridge 224 is adapted to contain a sample stabilizer 80 to provide passive and fast mixing of a blood sample 12 with the sample stabilizer 80. The sample stabilizer 80, can be an anticoagulant, or a substance designed to preserve a specific element within the blood such as, for example, RNA, protein analyte, or other element. In one embodiment, the sample stabilizer 80 is heparin or EDTA. In one embodiment, a plurality of biological fluid collection devices 200 could include different sample stabilizers. A biological fluid collection device 200 of the present disclosure provides flexibility in the nature of the additives and/or sample stabilizers introduced for a blood sample. The sample stabilizer 80 may be provided within a portion of the cartridge flow channel 254.

In one embodiment, the flow channel 254 may also include agitation members 81. The agitation members 81 can control a flow pattern of the blood sample 12 to induce mixing of the blood sample 12 and the sample stabilizer 80. In one embodiment, the agitation members 81 can be in the form of a flute or rib that is co-molded with the flow channel 254 and the sample stabilizer 80 can be coated on the flutes and/or on an inner sidewall surface 282 of the flow channel 254.

In one embodiment, the cartridge 224 of the biological fluid collection device 200 of the present disclosure is adapted to receive a blood sample 12 having a cellular portion 14 and a plasma portion 16. After collecting the blood sample 12, the cartridge 224 is able to separate the plasma portion 16 from the cellular portion 14. After separation, the cartridge 224 is able to transfer the plasma portion 16 of the blood sample 12 to a point-of-care testing device.

Referring to FIG. 20, in one embodiment, the cartridge 224 includes a blood separation element or separation member 284 disposed at least partially within a portion of the cartridge flow channel 254, for example, the reservoir 256. The blood separation element 284 is adapted to trap the cellular portion 14 of the blood sample 12 within the flow channel 254 and allow the plasma portion 16 of the blood sample 12 to pass through the blood separation element 284 to the port 250.

The blood separation element 284 may include commercially available hollow fiber membrane filters, or flat membrane filters, such as track-etch filters, also commercially available. Membrane filter pore size and porosity can be chosen to optimize separation of clean (i.e., red blood cell free, white blood cell free, and platelet free) plasma in an efficient manner. In another embodiment, the blood separation element 284 includes a lateral flow membrane. In other embodiments, the blood separation element 284 may comprise any filter that is able to trap the cellular portion 14 of the blood sample 12 within the flow channel 254 and allow the plasma portion 16 of the blood sample 12 to pass through the blood separation element 284 to the port 250.

Referring to FIG. 18, with the cartridge 224 disconnected from the housing 220, the port 250 is adapted for connection to a point-of-care testing device 90 for closed transfer of at least a portion of the multi-component blood sample 12 from the cartridge 224 to the point-of-care testing device 90.

Referring to FIGS. 13-21, use of a biological fluid collection device 200 of the present disclosure will now be described. Upon selecting a site, a user, an operator, or a clinician may position the housing 220 of the biological fluid collection device 200 over a selected sampling site, as shown by FIG. 16.

A user may then actuate or activate the puncturing element 222 to move the puncturing element 222 from the pre-actuation position (FIG. 21) to the puncturing position (FIG. 22) thereby causing the lancing of the skin surface S of the patient by the puncturing end 274 as shown in FIG. 22. In this manner, the puncturing end 274 cuts into the skin surface S of the patient's body and capillary blood begins to flow.

Referring to FIGS. 21 and 22, the housing 220 and the puncturing element 222 are part of a contact activated lancet device 246. To actuate the puncturing element 222 of a contact activated lancet device 246, the user needs only to place the housing 220 against a skin surface S and then exert a downwardly directed force on the housing 220 forcing the puncturing element 222 against skin surface S.

Referring to FIG. 17, once blood is flowing, the port 250 of the cartridge 224 is placed adjacent the blood of the skin surface S of the patient's body. In one embodiment, the port 250 of the cartridge 224 includes a vented portion that pulls off a first drop of blood. Once the cartridge 224 is filled with a blood sample 12, the clinician can remove the cartridge 224 from the housing 220.

In some embodiments, the cartridge 224 of the biological fluid collection device 200 can be used to separate the plasma portion 16 from the cellular portion 14 of the blood sample 12 using the blood separation element 284 and the blood sample 12 can be mixed with a sample stabilizer 80 as described above.

Referring to FIG. 18, after the blood sample 12 is stabilized and separated, the cartridge 224 may be engaged with a blood testing device or point-of-care testing device 90 for closed transfer of a portion of the homogenously stabilized blood sample from the biological fluid collection device 200 to the blood testing device or point-of-care testing device 90. The blood testing device 90 is adapted to receive the homogenously stabilized blood sample to analyze the homogenously stabilized blood sample and obtain test results.

With cartridge 224 engaged with a blood testing device 90, a user may depress the actuation member 268 to move the actuation member 268 to an activated position in which the multi-component blood sample 12 is expellable from the port 250 of the cartridge 224 to the blood testing device 90. For example, the port 250 may be placed over a receiving port 92 of the point-of-care testing device 90. Next, a clinician may transfer a portion of a blood sample 12, e.g., a plasma portion 16 of the blood sample 12, to the point-of-care testing device 90 in a closed manner, reducing exposure to the clinician and the patient. The point-of-care testing device 90 is adapted to receive the port 250 of the cartridge 224 for closed transfer of a portion of the plasma portion 16 of the blood sample 12 from the cartridge 224 to the point-of-care testing device 90. The point-of-care testing device 90 is adapted to receive the plasma portion 16 to analyze the blood sample and obtain test results.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
   a housing having a sidewall, a top wall, a bottom wall, a receiving port extending in a radial direction of the housing and defined between the top wall and the bottom wall, a housing flow channel, and an inlet port, the housing flow channel in fluid communication with the inlet port;
   a puncturing element at least partially disposed within the housing and transitionable between a pre-actuated position wherein the puncturing element is retained within the housing and a puncturing position wherein at least a portion of the puncturing element extends through the inlet port of the housing for establishing fluid communication with the housing flow channel; and
   a cartridge removably connectable to the receiving port of the housing between the top wall and the bottom wall, the cartridge defining a cartridge flow channel therein,
   wherein the cartridge comprises a pair of resiliently deflectable arms releasably engagable with and removable from the receiving port of the housing for securing the cartridge to the housing,
   wherein each of the pair of arms includes a base that engages an interference surface disposed within the receiving port and a free end extending away from the receiving port,
   wherein, upon deflection of the free end of the arms, the engagement between the base and the interference surface is released and the cartridge is disconnected and removable from the housing,
   wherein, with the cartridge connected to the housing, the cartridge flow channel is in fluid communication with the housing flow channel, and
   wherein, with the cartridge disconnected from the housing, the cartridge flow channel is sealed.

2. The biological fluid collection device of claim 1, further comprising a sample stabilizer disposed within a portion of the cartridge flow channel.

3. The biological fluid collection device of claim 1, wherein the housing flow channel of the biological fluid collection device is adapted to receive a multi-component blood sample having a cellular portion and a plasma portion.

4. The biological fluid collection device of claim 3, further comprising a separation member disposed at least partially within a portion of the cartridge flow channel, the separation member adapted to restrain the cellular portion and allow the plasma portion to pass therethrough.

5. The biological fluid collection device of claim 3, wherein the cartridge includes a cartridge inlet port in fluid communication with the housing flow channel when the cartridge is received within the receiving port of the housing and a transfer port in fluid communication with the cartridge flow channel.

6. The biological fluid collection device of claim 5, wherein with the cartridge disconnected from the receiving port, the transfer port is adapted for connection to a point-of-care testing device for transferring at least a portion of the multi-component blood sample from the cartridge to the point-of-care testing device.

7. The biological fluid collection device of claim 6, wherein the cartridge includes an actuation member in fluid transfer communication with the transfer port, the actuation member transitionable between an initial position in which the multi-component blood sample is stored within the cartridge and an activated position in which at least a portion of the multi-component blood sample is expelled from the transfer port.

8. The biological fluid collection device of claim 5, wherein the cartridge further comprises a valve disposed in fluid communication with the transfer port, the valve being transitionable between a closed position in which the transfer port is sealed and an open position in which a portion of a multi-component blood sample is adapted to pass therethrough.

9. The biological fluid collection device of claim 1, wherein the cartridge flow channel has a serpentine shape.

10. The biological fluid collection device of claim 1, wherein a portion of the cartridge includes electronic or machine readable information.

11. The biological fluid collection device of claim 10, wherein the electronic or machine readable information comprises a barcode.

\* \* \* \* \*